United States Patent [19]

Smith et al.

[11] Patent Number: 5,185,125

[45] Date of Patent: Feb. 9, 1993

[54] DENTAL ALLOY AND AMALGAM THEREOF

[75] Inventors: Susan L. Smith, Saline; Richard W. Fountain, Pinckney, both of Mich.

[73] Assignee: Special Metals Corporation, New Hartford, N.Y.

[21] Appl. No.: 801,290

[22] Filed: Dec. 2, 1991

[51] Int. Cl.⁵ ........................... C22C 5/06; C22C 5/00
[52] U.S. Cl. ................................. 420/503; 420/504; 420/589; 433/228.1
[58] Field of Search ....................... 420/503, 504, 589; 433/228.1

[56] References Cited

U.S. PATENT DOCUMENTS 4,374,085 2/1983 Asgar et al. .................. 420/503
4,664,629 5/1987 Chodkowski .................. 420/503

*Primary Examiner*—Deborah Yee
*Attorney, Agent, or Firm*—Robert F. Dropkin

[57] ABSTRACT

A dental alloy having, upon amalgamation, a desirable combination of physical properties and both a desirable condense time and carve time. The alloy contains from 48.75 to 50.75% silver, 20.25 to 21.75% copper, 28.25 to 29.25% tin, 0.05 to 0.8% palladium and up to 2.7% of elements selected from the group consisting of zinc, indium, manganese, cadmium, aluminum, gallium, ruthenium and mercury.

14 Claims, No Drawings

DENTAL ALLOY AND AMALGAM THEREOF

The present invention relates to an alloy, and in particular, an amalgamable dental alloy; and to an amalgam formed therefrom.

Dental amalgams are prepared in dental offices by reacting an amalgamable alloy with mercury. One such alloy is comprised of silver and tin. The reaction products are silver-mercury, tinmercury and some unreacted silver-tin powder, respectively known to those skilled in the art as $\gamma_1$, $\gamma_2$ and $\gamma$ phases. Tin-mercury ($\gamma_2$) is the weakest and least corrosion resistant of these phases.

U.S. Pat. No. 4,374,085 discloses a dental alloy characterized by good physical properties, superior corrosion resistance and the substantial absence of $\gamma_2$. The alloy is comprised of silver, tin, copper and palladium. Copper is present for its effect in eliminating $\gamma_2$. Palladium is present as it improves the alloy's corrosion resistance. Palladium has also been shown to reduce creep under a given load and temperature. The life of a dental restoration generally increases as creep values decrease.

An admixed type of dental material incorporating the alloy of U.S. Pat. No. 4,374,085 is disclosed in U.S. Pat. No. 4,664,629. This dental material contains both cut and spherical particles.

Some dentists have been reluctant to use the dental materials of U.S. Pat. Nos. 4,374,085 and 4,664,629 due to the lengthy times involved in completing their work. Dental material should be characterized by both a condense time (defined hereinbelow) and a carve time (defined hereinbelow) which are long enough to complete the restoration, but not too long. After all, a dentist's most valuable asset is his time.

Dentists require a certain period of time to complete a restoration. This time, known as work time, is composed of two parts. The first, or condense time, is the period from amalgamation to that time when the material is substantially unmoldable and loses its plasticity. The second, or carve time is the period from amalgamation to the time when the material will chip rather than cut or carve smoothly.

Through the present invention there is provided a dental alloy having the desirable combination of properties of the alloy of U.S. Pat. No. 4,374,085 and, upon amalgamation, both a desirable condense time and carve time. This is accomplished by controlling the tin content of the alloy within a very narrow range.

It is accordingly an object of the present invention to provide an alloy, and in particular, an amalgamable dental alloy; and an amalgam formed therefrom.

The alloy of the present invention consists essentially of, by weight, 48.75 to 50.75% silver, 20.25 to 21.75% copper, 28.25 to 29.25% tin, 0.05 to 0.8% palladium and up to 2.7% of elements selected from the group consisting of zinc, indium, manganese, cadmium, aluminum, gallium, ruthenium and mercury. A preferred silver content is from 49.25 to 50.25%. A preferred copper content is from 20.5 to 21.35%. A preferred tin content is from 28.5 to 29.0%. A preferred palladium content is from 0.25 to 0.65%. The alloy is usually present as an atomized powder.

Tin is maintained within the range of from 28.25 to 29.25% to obtain both a desirable condense time and a desirable carve time. Although these times are somewhat subjective depending upon the operator, the alloy of the present invention is deemed to have a condense time of from 2.5 to 3 minutes and a carve time of from 4 to 5.5 minutes. Subjective differences should be less than fifteen seconds.

The amalgam of the present invention is formed by triturating from 37 to 48% of mercury with from 52 to 63% of the dental alloy. Triturating is performed in accordance with procedures well known to those skilled in the art. Mercury is usually present in amounts of from 40 to 46%.

The following examples are illustrative of the invention:

EXAMPLE 1

Four alloys (Alloys A through D) were atomized. The composition of the alloys appear hereinbelow in Table I.

TABLE I

| Alloy | COMPOSITION (wt. %) | | | |
|---|---|---|---|---|
| | Ag | Sn | Cu | Pd |
| A. | 50.5 | 28.0 | 21.0 | 0.5 |
| B. | 49.75 | 28.5 | 21.25 | 0.5 |
| C. | 49.75 | 29.0 | 20.75 | 0.5 |
| D. | 49.5 | 29.6 | 20.4 | 0.5 |

Alloy A was heat treated at 310° F., triturated with 44% mercury and tested. It was solid at the end of trituration. It had virtually no condense time.

Another sample of alloy A was heat treated at 450° F., triturated with 44% mercury and tested. It had a condense time of 1.25 minutes and a carve time of less than 2 minutes.

Neither sample of Alloy A satisfied the criteria of the subject invention. They did not have a condense time of from 2.5 to 3 minutes and a carve time of from 4 to 5.5 minutes.

Four embodiments of Alloy B (Alloys $B_1$ through $B_4$) were triturated with 44% mercury and tested. Alloys $B_1$ through $B_4$ differed as to heat treating temperatures. Their respective heat treating temperatures appear hereinbelow in Table II along with their condense and carve times.

TABLE II

| Alloy | Heat Treating Temperature (°F.) | Condense Time (minutes) | Carve Time (minutes) |
|---|---|---|---|
| $B_1$ | 330 | less than 1 | 3 |
| $B_2$ | 350 | 2.5–3 | 4.5 |
| $B_3$ | 370 | 3 | 4–4.5 |
| $B_4$ | 390 | 3 | 5 |

Alloys $B_2$, $B_3$, and $B_4$ satisfied the criteria of the subject invention. They had a condense time of from 2.5 to 3 minutes and a carve time of from 4 to 5.5 minutes.

Five embodiments of Alloy C (Alloys $C_1$ through $C_5$) were triturated with 44% mercury and tested. Alloys $C_1$ through $C_5$ differed as to heat treating temperatures. Their respective heat treating temperatures appear hereinbelow in Table III along with their condense and carve times.

TABLE III

| Alloy | Heat Treating Temperature (°F.) | Condense Time (minutes) | Carve Time (minutes) |
|---|---|---|---|
| $C_1$ | 300 | 2–2.5 | 3 |
| $C_2$ | 310 | 3 | 5–5.5 |
| $C_3$ | 330 | 4.5 | 6 |
| $C_4$ | 350 | 5.5 | 7.5 |

TABLE III-continued

| Alloy | Heat Treating Temperature (°F.) | Condense Time (minutes) | Carve Time (minutes) |
|---|---|---|---|
| $C_5$ | 370 | 6.5 | 8.5 |

Alloy $C_2$ satisfied the criteria of the subject invention. It had a condense time of from 2.5 to 3 minutes and a carve time of from 4 to 5.5 minutes.

Alloy D was heat treated at 290° F., triturated with 42% mercury and tested. The alloy had a condense time of from 4 to 4.5 minutes and a carve time of from 6.5 to 7 minutes. It did not satisfy the criteria of the present invention. Alloy D did not have a condense time of from 2.5 to 3 minutes and a carve time of from 4 to 5.5 minutes.

The two alloys which satisfied the criteria of the subject invention had a tin content of from 28.25 to 29.25%. Alloy B had a tin content of 28.5%. Alloy C had a tin content of 29.0%.

EXAMPLE 2

Another alloy (Alloy E) was atomized. The composition of the alloy appears hereinbelow in Table IV.

TABLE IV

| Alloy | COMPOSITION (wt. %) | | | |
|---|---|---|---|---|
| | Ag | Sn | Cu | Pd |
| E | 49.75 | 28.75 | 21.0 | 0.5 |

Alloy E has a tin content (28.75%) within the preferred range for the subject invention.

Alloy E was heat treated at 350° F., triturated with 44% mercury and tested. It had a condense time of 3 minutes and a carve time of from 5 to 5.5 minutes. It, accordingly, satisfied the criteria of the subject invention.

The physical properties of Alloy E were evaluated. They appear hereinbelow in Table V.

TABLE V

| Alloy | Eames Time (minutes) | Properties | | | | |
|---|---|---|---|---|---|---|
| | | 1 Hour Compressive Strength (psi) | 24 Hours Compressive Strength (psi) | 7 Day Compressive Strength (psi) | Creep 7 Day (%) | 24 Hour Dimensional Change (microns) |
| E | 2.5–<3 | 49,899 | 70,388 | 77,310 | 0.011 | −1.4 |

The physical properties of Alloy E compare favorably with the alloys of U.S. Pat. Nos. 4,374,085 and 4,664,629. Eames Time is roughly comparable to the term, condense time, referred to frequently herein. The Eames test is set forth in a publication: Eames, W. B., and Skinner, E. W., 1965 International Association for Dental Research Program and Abstracts of Papers, page 60.

EXAMPLE 3

Another alloy (Alloy F) was atomized. The composition of the alloy appears hereinbelow in Table VI.

TABLE VI

| Alloy | COMPOSITION (wt. %) | | | |
|---|---|---|---|---|
| | Ag | Sn | Cu | Pd |
| F | 50.0 | 28.75 | 20.0 | 1.25 |

Alloy F is outside the subject invention despite the fact that it has a tin content within the range of the subject invention. It has a palladium content of 1.25%. The subject invention has a palladium content of from 0.05 to 0.8%.

Five embodiments of Alloy F (Alloys $F_1$ through $F_5$) were triturated with 44% mercury and tested. Alloys $F_1$ through $F_5$ differed as to heat treating temperatures. Their respective heat treating temperatures appear hereinbelow in Table VII along with their condense and carve times. Two values for each alloy are present.

TABLE VII

| Alloy | Heat Treating Temperature (°F.) | Condense Time (minutes) | Carve Time (minutes) |
|---|---|---|---|
| $F_1$ | 310 | less than 1 | not detectable |
| $F_1$ | 310 | less than 1 | less than 1 |
| $F_2$ | 330 | 2 | 5–5.5 |
| $F_2$ | 330 | less than 1 | 5–5.5 |
| $F_3$ | 340 | 3 | 7–7.5 |
| $F_3$ | 340 | 3 | 7–7.5 |
| $F_4$ | 350 | 2.5 | 7–7.5 |
| $F_4$ | 350 | 3.5 | 7–7.5 |
| $F_5$ | 390 | 3.5 | 8–8.5 |
| $F_5$ | 390 | 4.5–5 | 8–8.5 |

Alloys $F_1$ through $F_5$ did not satisfy the criteria of the subject invention. They did not have a condense time of from 2.5 to 3 minutes and a carve time of from 4 to 5.5 minutes.

It will be apparent to those skilled in the art that the novel principles of the invention disclosed herein in connection with specific examples thereof will suggest various other modifications and applications of the same. It is accordingly desired that in construing the breadth of the appended claims they shall not be limited to specific examples of the invention described herein.

We claim:

1. An amalgamable dental alloy consisting essentially of, by weight, 48.75 to 50.75% silver, 20.25 to 21.75% copper, 28.25 to 29.25% tin, 0.05 to 0.8% palladium and up to 2.7% of elements selected from the group consisting of zinc, indium, manganese, cadmium, aluminum, gallium, ruthenium and mercury; said amalgamable dental alloy having a condense time of from 2.5 to 3 minutes and a carve time of from 4 to 5.5 minutes upon amalgamation.

2. An alloy according to claim 1, having 28.5 to 29.0% tin.

3. An alloy according to claim 1, having 49.25 to 50.25% silver.

4. An alloy according to claim 1, having 20.5 to 21.35% copper.

5. An alloy according to claim 1, having 0.25 to 0.65% palladium.

6. An alloy according to claim 1, having 49.25 to 50.25% silver, 20.5 to 21.35% copper, 28.5 to 29.0% tin and 0.25 to 0.65% palladium.

7. An amalgam formed from 37 to 48% of mercury and 52 to 63% of a dental alloy; said dental alloy consisting essentially of, by weight, 48.75 to 50.75% silver, 20.25 to 21.75% copper, 28.25 to 29.25% tin, 0.05 to 0.8% palladium and up to 2.7% of elements selected from the group consisting of zinc, indium, manganese, cadmium, aluminum, gallium, ruthenium and mercury; said amalgam having a condense time of from 2.5 to 3 minutes and a carve time of from 4 to 5.5 minutes.

8. An amalgam according to claim 7, wherein said dental alloy has 28.5 to 29.0% tin.

9. An amalgam according to claim 7, wherein said dental alloy has 49.25 to 50.25% silver.

10. An amalgam according to claim 7, wherein said dental alloy has 20.5 to 21.35% copper.

11. An amalgam according to claim 7, wherein said dental alloy has 0.25 to 0.65% palladium.

12. An amalgam according to claim 7, wherein said dental alloy has 49.25 to 50.25% silver, 20.5 to 21.35% copper, 28.5 to 29.0% tin and 0.25 to 0.65% palladium.

13. An amalgam according to claim 7, formed from 40 to 46% mercury.

14. An amalgam according to claim 13, wherein said dental alloy has 49.25 to 50.25% silver, 20.5 to 21.35% copper, 28.5 to 29.0% tin and 0.25 to 0.65% palladium.

* * * * *